United States Patent [19]

Griffin, Jr.

[11] 4,031,014

[45] June 21, 1977

[54] METHOD OF REDUCING FRICTION LOSS

[75] Inventor: Thomas J. Griffin, Jr., Sand Springs, Okla.

[73] Assignee: The Dow Chemical Company, Midland, Mich.

[22] Filed: June 22, 1976

[21] Appl. No.: 698,666

Related U.S. Application Data

[63] Continuation-in-part of Ser. No. 656,675, Feb. 9, 1976.

[52] U.S. Cl. .............................. 252/8.55 R; 44/76; 137/13; 166/308; 252/1; 252/32.5; 252/89 R; 260/980

[51] Int. Cl.$^2$ ........................................ C09K 3/00

[58] Field of Search ............ 173/13; 252/1, 8.55 R; 260/980

[56] References Cited

UNITED STATES PATENTS

| | | | |
|---|---|---|---|
| 1,944,530 | 1/1934 | Schonburg | 260/950 |
| 2,005,619 | 6/1935 | Graves | 260/950 X |
| 3,484,474 | 12/1969 | Krause | 260/950 X |

Primary Examiner—Leland A. Sebastian
Attorney, Agent, or Firm—Bruce M. Kanuch; G. H. Korfhage

[57] ABSTRACT

The reaction product of a hydroxy ether and a pentavalent phosphorous compound with a short chain and/or long chain alcohol can be employed to reduce friction loss of organic liquids flowing through a confining conduit by mixing the reaction product with the organic liquid in the presence of a basic multivalent metal salt activator.

27 Claims, No Drawings

METHOD OF REDUCING FRICTION LOSS

CROSS-REFERENCE TO RELATED APPLICATION

This is a continuation-in-part of application Ser. No. 656,675 filed Feb. 9, 1976.

BACKGROUND OF THE INVENTION

This invention relates to improved methods of reducing friction losses of organic based liquids flowing through confining conduits such as in internal combustion engines, fracturing fluids employed to treat Subterranean formation, metal working fluid and the like. Representative art relating to these types of compounds, their preparation and use are found in U.S. Pat. Nos. 2,245,649; 2,274,302; 2,329,707; 2,346,155; 2,885,417; 2,905,683; 2,983,678; 2,983,679; 3,010,903; 3,331,896; 3,470,222; 3,494,949; 3,505,374; 3,547,820; 3,575,859; 3,706,822; 3,584,087 and 3,757,864, the teachings of which are specifically incorporated herein by reference.

Organic phosphoric acid esters have been employed in their free acid form and/or salts thereof as detergents, lubricating liquids, corrosion inhibitors, friction reducing agents, thickening agents and the like.

U.S. Pat. No. 3,757,864 teaches that certain aluminum salts of organic phosphoric acid esters are useful as friction reducing and gelling agents for nonpolar organic liquids. The salts are formed by reacting a basic aluminum compound with an ester which has been formed by reacting one or more monohydric aliphatic alcohols with a phosphorous compound such as $P_2O_5$, phosphorous oxychloride, $PCl_5$, $PF_5$ and the like.

It has now been discovered that certain metal salts of complex reaction products of a hydroxy ether and a phosphorous compound such as $P_2O_5$ are at least as effective as, and in many instances more effective than, the agents disclosed in U.S. Pat. No. 3,757,864 to reduce friction loss of refined oils and certain crude oils flowing through a confining conduit.

SUMMARY OF THE INVENTION

The product employed in the present invention is formed by reacting an essentially anhydrous hydroxy ether of the formula $ROR_1OH$ wherein R is a $C_1$ to $C_6$ alkyl group, $R_1$ is a $C_2$ or $C_3$ alkylene group and the total carbon atoms of $R_1$ and R range from 3 to about 8 with a pentavalent phosphorous compound which is substantially free from acid groups such as Cl, F and the like. When the total carbon atoms in the hydroxy ether is three or four, there is also reacted with the hydroxy ether and phosphorous compounds a long chain aliphatic monohydric alcohol containing at least five carbon atoms. A short chain aliphatic monohydric alcohol ($C_1$-$C_4$) can also be reacted therewith if desired. When the total carbon atoms in the hydroxy ether is five or more, there is reacted with the hydroxy ether and phosphorous compound either a long chain aliphatic alcohol (at least five carbons) or a short chain aliphatic monohydric alcohol ($C_1$-$C_4$) or a mixture thereof.

The above defined compounds are reacted with a pentavalent phosphorous compound for a period of time ranging from about 1.5 to about 6 hours at a temperature ranging from about 70° to about 90° C to form the novel complex reaction product of the present invention. As more fully described hereinafter, reaction products having different selected characteristics can be prepared by reacting specific reactants and by varying the order in which they are reacted together.

As a friction reducing agent the reaction product is dispersed into an organic liquid along with a basic salt containing a multivalent cation in an amount and specific ratio to each other to impart to the organic liquid a desired reduction in friction loss.

The gelled organic liquid can be employed as a fracturing fluid, as a carrying liquid for solids, and other utilities where organic liquids having favorable flow characteristics, i.e., reduction in friction loss, is useful.

DETAILED DESCRIPTION OF THE INVENTION

The short chain aliphatic monohydric alcohol can be branched or straight chained, primary, secondary, or tertiary and preferably is saturated. The preferred short chain alcohols are primary, straight chained, saturated alcohols. One or more can be employed. Specific alcohols which can be employed include, for example, methanol, ethanol, isopropyl alcohol, n-butyl alcohol, sec-butyl alcohol, tert-butyl alcohol and various mixtures thereof. Ethanol and methanol are preferred.

The long chain aliphatic monohydric alcohol can be saturated or unsaturated, branched or straight chained and can be a primary, secondary, or tertiary alcohol. The alcohol contains at least 5 carbon atoms and preferably from 5 to 12 carbon atoms. Examples of suitable alcohols include hexanol, decanol, oleyl alcohol, isooctyl alcohol, dodecanol, 4-decanol, triethylcarbinol, 3-ethyl-3-hexanol, 4-ethyl-3-hexanol and other similar alcohols. Mixtures of various alcohols are also suitable such as certain commercially available mixtures like, for example, AlFOL 810, AlFOL 610 and AlFOL 1012 from Continental Oil Company. The number indicates a mixture of alcohols containing from the lowest to highest number of carbon atoms. For example, AlFOL 810 is a mixture of saturated aliphatic alcohols containing $C_8$ and $C_{10}$ carbon atoms.

Suitable hydroxy ethers which can be employed include, for example, ethylene glycol monomethyl ether, ethylene glycol monoethyl ether, ethylene glycol mono-n-butyl ether, ethylene glycol mono-n-hexyl ether, ethylene glycol monoisobutyl ether, propylene glycol monoethyl ether, propylene glycol monoisobutyl ether, propylene glycol monomethyl ether, mixtures thereof and other like compounds.

The pentavalent phosphorous compound includes, for example, $P_2O_5$ and the like. $P_2O_5$ is preferred. A portion of the $P_2O_5$ may be replaced with a polyphosphoric acid solution; however, in the latter case polyphosphoric acid solutions containing an equivalent of at least about 83 percent by weight $P_2O_5$ are preferred. A maximum substitution of up to about 15 percent, preferably only up to about 10 percent by weight, of the $P_2O_5$ is possible since it is preferred that the reaction be conducted under essentially anhydrous conditions.

The order of addition of the reactants has not been found critical. One method comprises mixing the alcohols and hydroxy ether together and then slowly adding the phosphorous compound thereto with cooling of the reaction mixture to maintain the temperature below about 70° C. After complete addition of the phosphorous compound the temperature of the reaction is maintained at between 70° and 90° C, preferably 80° to 90° C, for from about 1.5 to about 6, preferably from about 1.5 to about 3 hours, but in any event for a sufficient time for the reaction to go to the desired degree of completion. These temperatures are for a reaction conducted at atmospheric pressures. The reaction mixture can be employed as is or as a concentrate in an organic liquid or freeze point depressant, such as an aromatic hydrocarbon or the like.

Where only the hydroxy ether and a short chain alcohol are employed as reactants it is especially preferred to first react the hydroxy ether with the phosphorous compound and then add the short chain alcohol.

The reactants should be reacted together in certain molar ratios to provide reaction products having the most favorable friction loss reducing characteristics. The molar ratios which are operable are set forth in the following table wherein $P_2O_5$ is the pentavalent phosphorous compound.

| Mole Ratio to $P_2O_5$ | Reactants Short Chain Alcohol | $ROR_1OH$ | Long Chain Alcohol |
|---|---|---|---|
| Operable | 0.5 to 5.0 | 0.4 to 4.5 | 0 to 4.0 |
| Preferred | 0.9 to 2.0 | 0.8 to 1.8 | 0 to 1.4 |

The mole ratio of the total of the short chain and/or long chain alcohol and the hydroxy ether to phosphorous pentoxide ranges from about 2.8:1 to about 7.0:1 with the most preferred ratio being about 3.64:1.

The reaction product is a complex mixture of phosphate esters the exact identity of which has not been determined. It has, however, been found that reaction products produced in an essentially identical manner will have essentially identical friction loss reducing properties.

Organic liquids which can be employed in the practice of the invention are generally non-polar and include, for example, aliphatic, and chlorinated hydrocarbons, and mixtures thereof, refined paraffinic oils, such as lubricating oils, kerosene, diesel oil, fuel oil and certain crude oils. The effectiveness and optimum quantities of reaction product to increase the viscosity of any particular organic liquid should be ascertained prior to a large scale use.

The reaction product is mixed with an organic liquid along with a basic salt containing a multivalent metal cation. By basic it is meant that an aqueous solution of the salt has a pH greater than 7.

Suitable basic salts containing a multivalent metal cation which can be employed include sodium aluminate (dry or in an aqueous solution), ferric nitrate, aluminum nitrate, and rare earth metal salts of the elements of atomic numbers 57-71. Preferred are aluminum salts such as sodium aluminate.

The reaction product and metal salt are employed in a total amount and weight ratio to each other to produce a product having desired friction loss characteristics. These amounts and ratios will vary and are dependent on the reactants which are employed to make the reaction product, the exact metal salt, the organic liquid employed, and the desired viscosity. For example, less than about 8 gallons of the phosphate ester can be employed per 1000 gallons of organic liquid with from about 0.01 to about 1.5 gallons of a 38 percent by weight of a sodium aluminate solution per 1000 gallons of organic liquid. For different quantities of phosphate ester the amount of metal salt will vary proportionally.

When the reaction product is employed to decrease the friction loss of an organic liquid which is to be employed as a fracturing fluid standard techniques of mixing and fracturing can be employed. For example, a suitable amount of a reaction product which has been previously prepared is mixed with, for example, kerosene or crude oil in a mixing tank along with a suitable basic metal compound. The so prepared fluid is then employed to fracture, for example, a petroleum producing formation employing standard equipment and techniques known in the art. In general, the method comprises pumping the so prepared fluid through a borehole and into contact with the subterranean formation to be fractured at a sufficient pressure to fracture the same. It is preferred to employ a sufficient amount of the reaction product and multivalent metal activator to reduce the friction pressure of the organic liquid flowing through the contemplated confining conduit by at least about 5 percent. Generally from 0.1 to 0.9 gallon of reaction product per 1000 gallons of organic liquid is suitable.

Various reaction products suitable for use in the practice of the present invention were prepared in the following manner.

Preparation of Alkyl Phosphates by Mixed Addition

The desired quantities of alcohol and hydroxy ether were placed in a reaction flask equipped with a mechanical stirrer, reflux condenser, thermometer and heating mantle. With continuous stirring, $P_2O_5$ was added, maintaining the temperatures below 70° C with cooling. After complete addition of $P_2O_5$, the mixture was heated to 80° C and maintained for six hours. The product was then cooled and formulated as described hereinafter.

Preparation of Alkyl Phosphates by Separate Addition

The procedure described directly hereinbefore was followed, except that the $P_2O_5$ was first added to the hydroxy ether, and if employed, a long-chain alcohol. After complete addition of the $P_2O_5$ and 15 minutes of mixing, the short-chain alcohol (methanol and/or ethanol) was added while the temperature of the reaction mixture was maintained below 50° C by controlled addition. The mixture was then heated to 80° C and reacted for six hours. The product was then cooled, and formulated as described hereinafter.

Preparation of Alkyl Phosphate Esters Employing Polyphosphoric Acid

The first procedure described above was followed except that after two hours at 80° C, the mixture was cooled to 50° C and a certain amount of polyphosphoric acid was added. The mixture was then heated to 80° C for an additional 3½ hours.

Formulation of Friction Reducing Agent

The products of the procedures described above were formulated into a premix by mixing 40.0 ml (77.3% by volume) of the ester reaction product with 11.7 ml (22.7% by volume) of an aromatic hydrocarbon solvent comprised primarily of a complex mixture of aromatics comprised of alkyl substituted benzenes and some alkyl substituted naphthalenes. The specifications of the aromatic solvent employed are: 18° API gravity; 90% minimum aromatics, 96% typical aromatics; 214° C initial boiling point; 334° C final boiling point. The premix is then mixed with an organic liquid and a suitable multivalent metal salt in an amount sufficient to reduce the friction-loss of the organic liquid.

What is claimed is:

1. A method of reducing the friction loss generated by an organic liquid flowing through a confining conduit which comprises:
   mixing up to about 0.9 gallon per 1000 gallons of said organic liquid of an organic phosphate ester reaction product comprising the reaction of
   a pentavalent phosphorous compound with a hydroxy ether of the formula $ROR_1OH$ wherein R is a $C_1$ to $C_6$ allyl group, $R_1$ is a $C_2$ or $C_3$ alkylene group and the total carbon atoms of R and $R_1$ range from 3 to about 8; and
   when the total carbon atoms of R and $R_1$ is 3 or 4, with a long chain monohydric aliphatic alcohol containing at least 5 carbon atoms; when the total carbon atoms of R and $R_1$ are five or more with an alcohol selected from the group consisting of a long chain monohydric aliphatic alcohol containing at least 5 carbon atoms, a short chain monohydric aliphatic alcohol containing from one to four carbon atoms or a mixture of said alcohols, said reaction being conducted at a temperature ranging from about 70 to about 90° C for a period of time of from about 1.5 to about 6 hours and a sufficient quantity of a basic salt containing a multivalent metal cation to provide friction reduction.

2. The method of claim 1 wherein the short chain alcohol is a primary, straight chain, saturated alcohol.

3. The method of claim 1 wherein the pentavalent phosphorous compound is $P_2O_5$.

4. The method of claim 1 wherein the long chain monohydric alcohol contains from 5 to about 12 carbon atoms.

5. The method of claim 1 wherein the short chain alcohol is ethanol, methanol or a mixture thereof.

6. The method of claim 1 wherein the individual mole ratios of the hydroxy ether, the long chain alcohol and the short chain alcohol to the pentavalent phosphorous compound are within the ranges of 0.4:1 to 4.5:1, 0:1 to 4.0:1 and 0.5:1 to 5.0:1 respectively.

7. The method of claim 6 wherein the total mole ratio of the hydroxy ether, the long chain alcohol and the short chain alcohol to the pentavalent phosphorous compound ranges from about 2.8:1 to 7.0:1.

8. The method of claim 1 wherein the individual mole ratios of the hydroxy ether, the long chain alcohol and the short chain alcohol to the pentavalent phosphorous compound are within the ranges of 0.8:1 to 1.8:1, 0:1 to 1,4:1; and 0.9:1 to 2.0:1 respectively.

9. The method of claim 8 wherein the total mole ratio of the hydroxy ether, the long chain alcohol and the short chain alcohol to the pentavalent phosphorous compound is about 3.64 to 1.

10. The method of claim 1 wherein when the total carbon atoms of R and $R_1$ is 3 or 4 there is also reacted a short chain aliphatic monohydric alcohol containing from 1 to 4 carbon atoms.

11. The method of claim 10 wherein the short chain alcohol is methanol or ethanol.

12. The method of claim 10 wherein the short chain alcohol is methanol.

13. The method of claim 1 wherein the multivalent metal is aluminum.

14. The method of claim 1 wherein the basic salt is sodium aluminate.

15. The method of claim 1 wherein said confining conduit comprises a wellbore.

16. A method of reducing the friction loss generated by an organic liquid flowing through a confining conduit which comprises mixing 0.9 gallon per 1000 gallons of said organic liquid of an organic phosphate ester reaction product comprising the reaction of,
   $P_2O_5$ with a hydroxy ether compound of the formula $ROR_1OH$ wherein R is a $C_1$ to $C_6$ alkyl group and $R_1$ is a $C_2$ or $C_3$ alkylene group and the total carbon atoms of R and $R_1$ ranges from 3 to about 8; and
   when the total carbon atoms of R and $R_1$ is 3 or 4 with a long chain aliphatic monohydric alcohol containing from 5 to about 12 carbon atoms, when the total carbon atoms of R and $R_1$ is 5 to 8, with an alcohol selected from the group consisting of a long chain monohydric aliphatic alcohol containing from 5 to about 12 carbon atoms, a short chain monohydric aliphatic alcohol containing from 1 to 4 carbon atoms or a mixture of said alcohols, the individual mole ratios of the hydroxy ether, the long chain alcohol and the short chain alcohol to $P_2O_5$ are within the ranges of 0.4:1 to 4.5:1; 0:1 to 4.0:1 and 0.5:1 to 5.0:1 respectively, said reaction being conducted at a temperature ranging from about 70° to about 90° C for a period of time of from about 1.5 to about 6 hours, and a sufficient basic salt containing a multivalent metal cation to provide friction reduction.

17. The method of claim 16 wherein the short chain alcohol is a primary, straight chain, saturated alcohol.

18. The method of claim 16 wherein the short chain alcohol is ethanol, methanol or a mixture thereof.

19. The method of claim 16 wherein the individual mole ratios of the hydroxy ether, the long chain alcohol and the short chain alcohol to $P_2O_5$ are within the ranges of 0.8:1 to 1.8:1; 0:1 to 1.4:1; and 0.9:1 to 2.0:1 respectively.

20. The method of claim 19 wherein the total mole ratio of the hydroxy ether, the long chain alcohol and the short chain alcohol to $P_2O_5$ ranges from about 2.8:1 to about 7.0:1.

21. The method of claim 16 wherein the short chain alcohol is methanol.

22. The method of claim 16 wherein the total mole ration of the hydroxy ether, the long chain alcohol and short chain alcohol to $P_2O_5$ is about 3.64 to 1.

23. The method of claim 16 wherein the reaction temperature ranges from about 80° to about 90° C and the reaction time ranges from about 1.5 to about 3 hours.

24. The method of claim 16 wherein when the total carbon atoms of $R_1$ is 3 or 4 there is also reacted methanol or ethanol.

25. The method of claim 16 wherein the multivalent metal is aluminum.

26. The method of claim 16 wherein the basic salt is sodium aluminate.

27. The method of claim 16 wherein the confining conduit is a wellbore.

* * * * *

UNITED STATES PATENT AND TRADEMARK OFFICE
CERTIFICATE OF CORRECTION

PATENT NO. : 4,031,014
DATED : June 21, 1977
INVENTOR(S) : Thomas J. Griffin, Jr.

It is certified that error appears in the above-identified patent and that said Letters Patent are hereby corrected as shown below:

Column 1, line 12, change the word "Subterranean" to --subterranean--.

Column 1, line 13, change "formation" to --formations-- and "fluid" to --fluids--.

Column 2, line 27, add --about-- before "12".

Column 2, line 64, add the word --mixture-- after "reaction".

Column 5, line 10, delete the word "allyl" and insert --alkyl--.

Column 5, Claim 8, line 49, delete "1,4:1 and insert --1.4:1--.

Column 6, Claim 16, line 7, insert --up to about-- after the word "mixing".

Column 6, Claim 22, line 48, delete "ration" and insert --ratio- and insert the word --the-- at the end of line 48.

Column 6, Claim 25, line 58, insert the word --cation-- after "metal".

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*